United States Patent
Pan et al.

(10) Patent No.: US 6,448,061 B1
(45) Date of Patent: Sep. 10, 2002

(54) **PTA LDHA DOUBLE MUTANT *ESCHERICHIA COLI* SS373 AND THE METHOD OF PRODUCING SUCCINIC ACID THEREFROM**

(75) Inventors: Jao Go Pan; Soo An Shin; Chan Kyu Park; Pil Kim; Dong Eun Chang; Jae Eun Kim, all of Taejeon (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 09/463,484

(22) PCT Filed: Jul. 31, 1998

(86) PCT No.: PCT/KR98/00235

§ 371 (c)(1),
(2), (4) Date: Jan. 27, 2000

(87) PCT Pub. No.: WO99/06532

PCT Pub. Date: Feb. 11, 1999

(30) Foreign Application Priority Data

Jul. 31, 1997 (KR) ............................................. 97-36590

(51) Int. Cl.[7] ........................ C12N 1/20; C12N 15/74; C12P 7/46; C07H 21/04
(52) U.S. Cl. .................. 435/252.33; 435/145; 435/471; 536/23.2; 536/23.1
(58) Field of Search ................................. 435/136–145, 435/252.1–252.35, 471; 536/23.2, 23.1, 23.7

(56) References Cited

PUBLICATIONS

Chatterjee et al., Applied and Environmental Microbiology, 67(1): 148–154, 2001.*
Stols and Donnelly, Appl. Environ. Microbiol. 63:2695–2701, 1997.*
Bauer et al., Appl. Environ. Microbiol. 56:1296–1302, 1990.*

* cited by examiner

*Primary Examiner*—Ponnathapu Achutamurthy
*Assistant Examiner*—Delia Ramirez
(74) *Attorney, Agent, or Firm*—McGuireWoods LLP

(57) ABSTRACT

This invention relates to a mutant *Escherichia coli* SS373 and the production of succinic acid by using the above strain. In detail, a novel *E. coli* SS373 (W3110 pta::Tn10 ldhA::Km) with the deficiency in the acetate and lactate forming pathways was constructed by genetic engineering technique. An aerobically grown SS373 was then cultured by means of the anaerobic condition shift during the succinate producing stage, which resulted in the efficient production of succinic acid with a higher yield.

4 Claims, 2 Drawing Sheets

VERTICAL LINE INDICATES THE TIME OF
ANAEROBIC SHIFT AND GLUCOSE (30g) ADDITION.

PTA LDHA DOUBLE MUTANT ESCHERICHIA COLI SS373 AND THE METHOD OF PRODUCING SUCCINIC ACID THEREFROM

BACKGROUND OF THE INVENTION

1. Field of the Invention

This invention relates to a mutant *Escherichia coli* SS373 and the production of succinic acid by using the above strain. In detail, a novel *E. coli* SS373 (W3110 pta::Tn10 ldhA::Km) with the deficiency in the acetate and lactate forming pathways was constructed by genetic engineering technique. An aerobically grown SS373 was then cultured by means of the anaerobic condition shift during the succinate producing stage, which resulted in the efficient production of succinic acid with a higher yield.

2. Description of the Prior Art

Succinate is one of the basic metabolites and an intermediate in the TCA cycle of the biological system. In the petrochemical industry, succinate serves a precursor of 1,4-butandiol. tetrahydrofuran, γ-butyrolactone. It is also useful as an ingredient in the food and cosmetic industry. Succinic acid is commercially produced by a chemical process. Recently the biological process has been of interest for an environmentally clean process. In addition. the biological process could produce succinate from low-cost renewable resources. For the reasons of as above, the biological succinate production has been intensely studied in the recent years. Among these studies, strict anaerobic *Anaerobiospirillum succiniciproducens* has been particularly well examined (U.S. Pat. Nos. 5,573,931, 5,521,075, 5,504,004). *A. succiniciproducens*, however, has a complex nutrient requirement and slows growth rate as well as difficulty in the production process associated with the strict anaerobe.

SUMMARY OF THE INVENTION

To solve the problems of a strict anaerobe in the succinate production, a facultative anaerobic *E. coli* was genetically engineered. By using the mutated *E. coli*, the succinate production with higher yield was achieved. Therefore, the objective of the invention herein is the construction of a mutant *E. coli* and enhanced production of succinate by using the mutant *E. coli*.

DETAILED DESCRIPTION OF THE INVENTION

Figure 1:
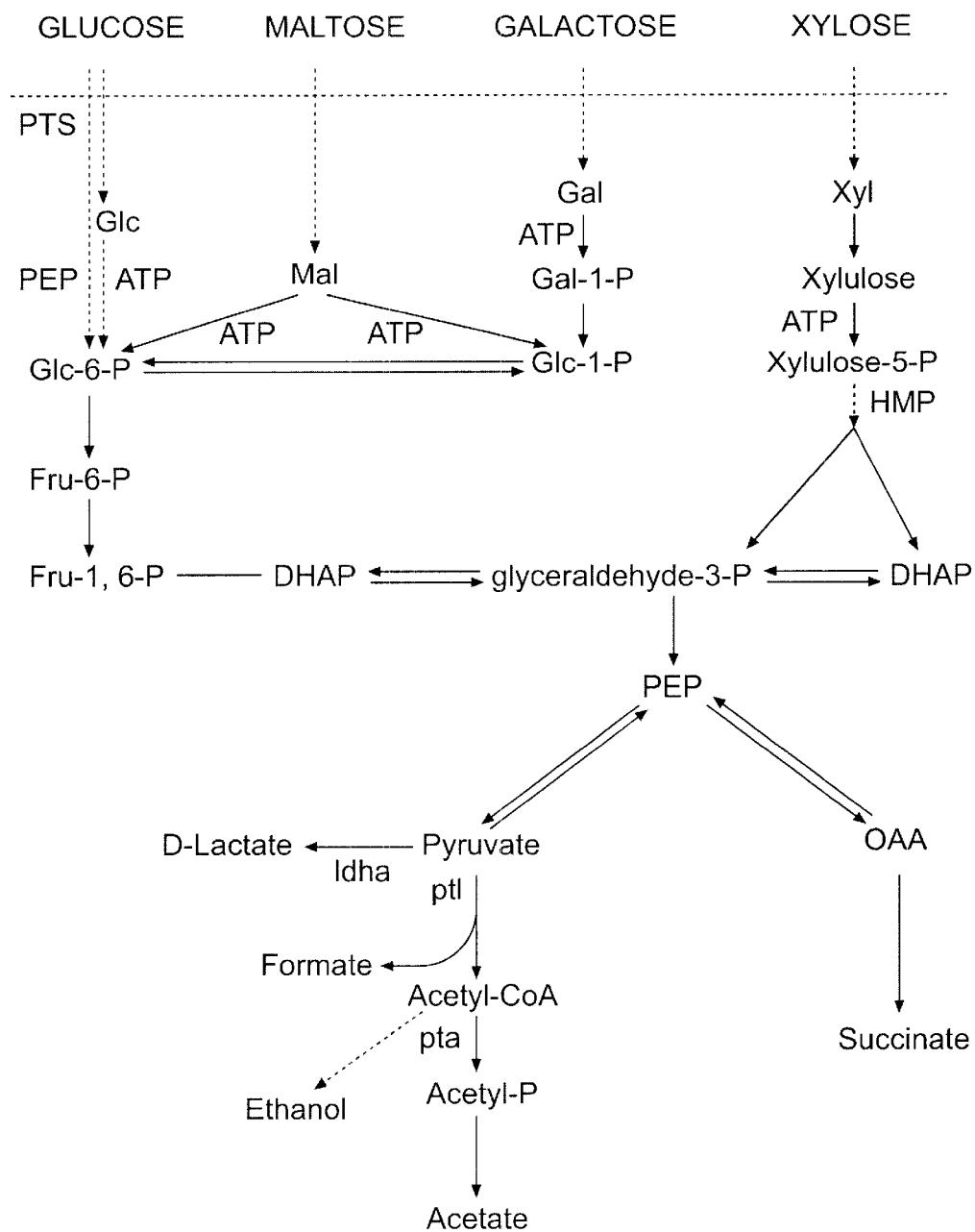
FIG. 1 represents the metabolic pathway of SS373 based on various carbon sources.

The invention herein is characterized by *Escherichia coli* SS373(W3110 pta::Tn10 ldhA::Km). The method of the anaerobic production of succinate after aerobic growth of cells is also involved. The detailed descriptions are as follows:

As reported in the Bergey's Manual, *E. coli* has the following characteristics: facultative anaerobe, rod shaped, Gram-positive, simple nutrient demand, fast growth rate (doubling time≈20 min.), temperature optimum of 37° C., and pH optimum of 7.0. Especially, *E. coli* yields a mixture of acetate, lactate, formate, succinate, and ethanol from glucose in the anaerobic condition. The physiology and genetics of *E. coli* have been well studied, and the *E. coli* metabolism could be easily controlled and estimated. In addition, the metabolic engineering could be readily applied by means of genetic engineering technique.

Principle of Succinate Mass-production

To produce succinate by using *E. coli*, an *E. coli* W3110 was modified genetically. The modified *E. coli* was further optimized to lead to an enhanced production.

Because *E. coli* carries out a mixed acid-fermentation, the metabolic pathway of *E. coli* should be altered to efficiently produce succinate. By means of the genetic block of the pathway involved in the other products. the succinate production would be improved. At first the genes of pta and ldhA of *E. coli*, which encode the first enzyme of acetate and lactate pathway, were mutated.

The constructed strain was cultured in an aerobic condition with high growth rate which in turn produced succinate in the anaerobic condition. The succinate therefrom is able to penetrate the cell membrane to accumulate in the medium which in turn prevents a feedback control of cells. The accumulated succinate can be recovered with high purity by electrodialysis technique (Hongo, M., *Appl. Environ. Microbiol.* 52–2 314–319 (1986)).

Construction of a Double Mutated *E. coli*

Construction of a double mutated *E. coli* was carried out by the method suggested by Silhavy.

Step 1. Preparation of Transformed P1 Phage

P1 lysates of a *E. coli* CP993 (pta::Tn10-lacZ1)(Shin, S. A. and C. K. Park. *J. Bacteriol.*, 177, 4696–4702 (1995)) and a *E. coli* NZN117 (ldhA::Km)(Bunch. P. K. et al. *Microbiology*, 143, 187–195 (1997)) were prepared respectively.

Step 2. P1 Transduction of the pta::Tn10-lacZ1 to W3110

An *E. coli* W3110 (*E. coli* genetic stock center collection number (CGSC) 4474) was used as a recipient strain. The insertion mutated gene (pta::Tn10-lacZ-1) of *E. coli* CP993was transferred to *E. coli* W3110 by P1 transduction. The mutant *E. coli* strains were selected on the tetracyclin selection plate which yielded an *E. coli* W3110 pta::Tn10-lacZ-1

Step 3. P1 Transduction of the ldhA::Km to W3110pta::Tn10-lacZ-1

To obtain a lactate-production deficient strain. P1 lysate of NZN1117 was infected with *E. coli* W3110 pta::Tn10-lacZ-1. The selected strain on the kanamycin plate was an double mutated W3110 pta::Tn10-lacZ-1 ldhA::Km.

Principle of Succinate Production in SS373 from Various Carbon-sources

Though the pathways to succinate slightly differ from one another depending on the carbon source, the phosphorylation is a common process (FIG. 1). In the case of glucose, which is the most common carbon source, the main phosphate donor has been known to be phosphoenolpyruvate (PEP) when glucose is transported by phosphate transferase system (PTS). The PEP involved in the glucose uptake converts to pyruvate, and the chance for the succinate production is relatively reduced because succinate is derived from oxaloacetate (OAA). Hence, the phosphate groups are delivered from ATP in the cases of galactose, xylose, and maltose, the PEP would be saved as compared with that of the case with glucose. The conservation of PEP, which serves as a phosphate donor in the PTS, would lead to the increase of succinate production as well as a decrease of by-product formation.

This invention will be described detail in the following examples but is not limited thereby.

EXAMPLE 1
Construction of a Double Mutated E. coli for the Succinate Production Step 1. Preparation of Transformed P1 Phage The P1 transduction was carried out by the Silhavy method. Each E. coli strain of pta::Tn10-lacZ-1 and ldhA::Km was pre-cultured in 3ml of TGC media (0.1% glucose, lacto-tryptone, 10 mM $CaCl_2$). The overnight grown cells were transferred to the 3 ml of TGC media and cultured for 1 hr at 35° C. in a shaking incubator. When the absorbance (600 nm) of cells was reached at 0.1, the P1 phage (30 μl in the concentration of 1010 pfu/ml) was infected and cultured for 2–3 hrs. After the cell lysis, chloroform (0 ml was added and then supernatant was prepared by centrifuge. The supernatant Step 2. P1 Transduction of the pta::Tn10-lacZ1 to W3110

The overnight grown E. coli W3110 was prepared by centrifuge. After the dispersion of cells with 0.5 ml of divalent ion solution (10 mM $MgSO_4$, 5 mM $CaCl_2$), the P1 lysate of pta::Tn10-lacZ-1 (0.01–0.1 ml) was appended. The mixture was left to stand for 15 minutes at room temperature. The cells were collected by centrifuge and then washed twice by 1 ml of 1M sodium citrate. After the activation in LB medium, the mutant cells were selected on the LB-agar plate containing tetracycline (13 μg/ml).

Step 3. P1 Transduction of the ldhA::Km to W3110 pta::Tn10-lacZ-1

The P1 lysate of ldhA::Km from step 1 was infected to the strain obtained from step 2. After the same procedure of step 2, a double mutant of W3110 pta::Tn10-lacZ-1 ldhA::Km was obtained on the LB-agar plate containing kanamycin (20 μg/ml).

The finally obtained E. coli W3110 pta::Tn10-lacZ-1 ldhA::Km was named E. coli SS373. The E. coli SS373 was deposited on the 28th of Jul. 1997 in the Korea Collection of Type Culture(KCTC; 52, Ereun-dong, Yusong-ku, Taejeon 305–333 Republic of Korea), which is an international strain deposit institute by ale Budapest Convention, and the deposit number was assigned as KCTC 8818P. For the purpose of PCT international application, a conversion of the original deposit under the Budapest Treaty was made on Jul. 29, 1998, and a new deposit number was obtained e.g. KCTC 0506BP.

The E. coli SS373 could be cultured on a glucose medium in an anaerobic condition because it could produce acetyl-CoA while E. coli NZN111(Clark D. P. FEMS Microbiol Rev., 63, 223–234 (1989)) could not.

EXAMPLE 2
Succinate Production in the Glucose Medium

The E. coli SS373 was cultured on a glucose-based medium. The components of medium were represented as Table 1.

TABLE 1

| Component | Glucose | $Na_2HPO_4$ · $H_2O$ | $NaH_2PO_4$ | Yeast Extract | $Na_2CO_3$ |
|---|---|---|---|---|---|
| Concentration (g/l) | 15 | 7 | 3 | 5 | 3.18 |

Note: The pH was pre-set to 7.0 by adding a few drops of conc. $H_2SO_4$.

Figure 2:
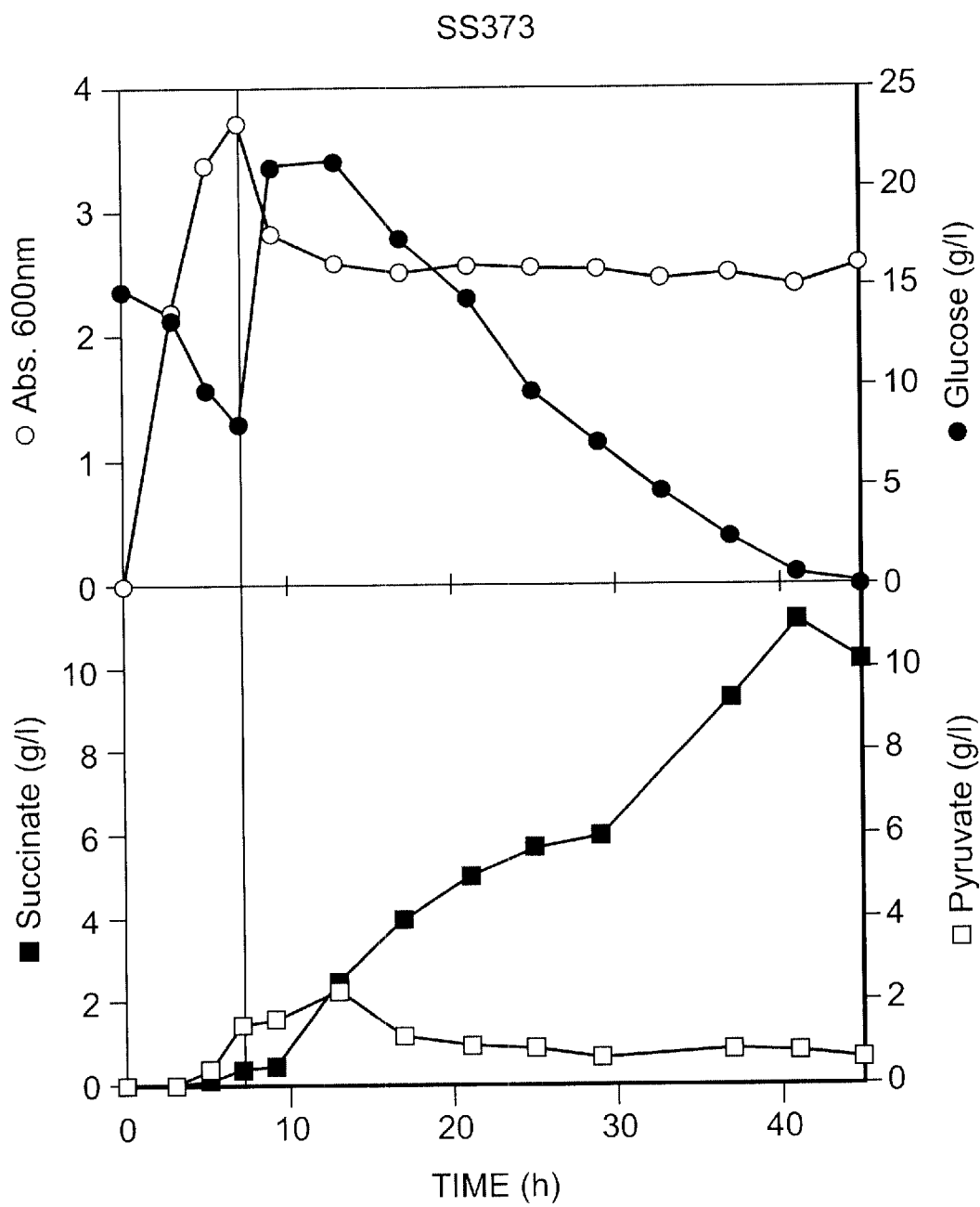
FIG. 2 indicates the succinate production profile by SS373.

A single colony of SS373 was sub-cultured in a 15 ml test tube at 37° C. for 12 hours. Cells were transferred to a 50 ml medium in 250 ml Erlenmeyer flask and cultured until absorbance reached 0.5 at 600 nm. The actively grown cells from above were inoculated to a 2.5-liter jar-fermentor containing 1-liter medium and cultured at 37° C., pH 7.0 in aerobic condition (350 rpm, 1 vvm). When the absorbance (600 nm) reached 4.0, aeration was stopped and mixed gas (5% $CO_2$, 95% $N_2$) was fluxed in. Upon shifting to anaerobic conditions, 500 ml of a glucose solution (60 g/l) was added. Thereafter, 11 g/l of succinate was produced with 0.8 g/l of pyruvate in 34 hours of culture. (FIG. 2)

The concentrations of succinate and pyruvate were estimated by using a HPLC-UV system (Gilson, France) with carbohydrate analysis column (HPX-87H, Bio-Rad). The glucose concentration was measured by the Glucose-Analyzer (2300STAT, Yellow Spring Instruments).

EXAMPLE 3
Succinate Productions Based on Various Carbohydrates

The E. coli SS373 and W3110 were cultured in the media containing different carbon sources (Table 2). The carbon sources used were glucose, galactose, maltose, and xylose, respectively.

TABLE 2

| Component | *Carbon source | $Na_2HPO_4$ · $H_2O$ | $NaH_2PO_4$ | Yeast Extract | $Na_2CO_3$ |
|---|---|---|---|---|---|
| Concentration (g/l) | 10 | 7 | 3 | 5 | 3.18 |

Note: The pH was set to 7.0 by adding a conc. $H_2SO_4$. *Carbon sources were glucose, galactose, maltose, and xylose, respectively.

A single colony of SS373 was sub-cultured in a 15 ml test tube at 37° C. for 12 hours. Cells were transferred to a 10 ml medium in 100 ml Erlenmeyer flask. The biomass was set to an approximate absorbance of 1.0 at 600 nm. The flask was flushed with 5% CO, gas and sealed by using a silicon stopper to maintain anaerobic condition. Cells were cultured for 8 hrs at 37° C. and organic acids formation were investigated (Table 3).

In the cases of wild strains, e.g., W3110, the major organic acids were lactate and acetate, while succinate and pyruvate were the major factors in the SS373. In the SS373, the proportions of succinate to pyruvate were varied depending on the carbon sources used. The glucose medium showed 1:2 of succinate to pyruvate with 1:0.8 for maltose and 1:0.3 for galactose and xylose. Nearly pure succinate was obtained in the concentration of 1.9 and 1.6 g/l from galactose and xylose, respectively. Therefore, the use of non-PTS carbohydrates was preferable in producing succinate with high purity and yield because PEP used in phosphorylation was conserved

TABLE 3

Effect of Carbon Sources on the Succinate Production in E.coli SS373

| Strain | Carbon source | Succinate (g/l) | Pyruvate (g/l) | Lactate (g/l) | Acetate (g/l) |
|---|---|---|---|---|---|
| W3110 | Glucose | 0.6 | 0 | 1.0 | 1.0 |
|  | Maltose | 0.5 | 0 | 1.6 | 1.6 |
|  | Galactose | 2.1 | 0 | 0.8 | 2.3 |
|  | Xylose | 1.6 | 0.2 | 0.9 | 1.6 |
| SS373 | Glucose | 2.7 | 5.3 | 0 | 0.6 |
|  | Maltose | 2.3 | 1.8 | 0 | 0.1 |
|  | Galactose | 1.9 | 0.6 | 0 | 0.3 |
|  | Xylose | 1.6 | 0.4 | 0 | 0.4 |

As noted, succinate in a novel E. coli SS373 could be produced with less effort to maintain strict anaerobic condition and without complex nutrient supply. In addition, E. coli SS373 showed fast growth rate due to the efficient succinate production. Moreover, nearly pure succinate could be produced by using a carbon source with the result of conserving PEP.

What is claimed is:

1. A phosphotransacetylase (pta) lactate dehydrogenase (ldhA) double mutant *E. coli* SS373 (KCTC 0506BP) which lacks the ability to produce lactate and acetate.

2. A method of producing succinic acid comprising the steps of:
   (a) culturing the pta ldhA double mutant *E coli* SS373 of claim 1 via a two-stage culture wherein *E. coli* SS373 is initially cultured under aerobic conditions for bacterial growth, and is subsequently cultured under anaerobic conditions for succinic acid production; and
   (b) recovering succinic acid from the culture medium.

3. The method of producing succinic acid according to claim 2, wherein said two-stage culture is performed in the presence of a substrate which does not require phosphoenolpyruvate for membrane transport.

4. A method of making a succinic acid-producing *E. coli* strain, wherein insertional mutations in the pta and ldhA genes result in a strain deficient in the production of lactate and acetate, and enhanced production of succinic acid.

* * * * *

UNITED STATES PATENT AND TRADEMARK OFFICE
CERTIFICATE OF CORRECTION

PATENT NO. : 6,448,061 B1
DATED : September 10, 2002
INVENTOR(S) : Young Sub Oh et al.

It is certified that error appears in the above-identified patent and that said Letters Patent is hereby corrected as shown below:

<u>Title page,</u>
Item [75], Inventors, the name of the first inventor should be corrected to
-- Jae Gu Pan --.

Signed and Sealed this

Third Day of December, 2002

JAMES E. ROGAN
*Director of the United States Patent and Trademark Office*